United States Patent [19]
Glass et al.

[11] Patent Number: 5,338,727
[45] Date of Patent: Aug. 16, 1994

[54] THERAPEUTIC AGENT FOR THE PREVENTION OR TREATMENT OF ADULT RESPIRATORY DISTRESS SYNDROME

[75] Inventors: Mitchell Glass, Wilmington, Del.; Joseph C. Williams, Elkton, Md.; Ross L. Stein, Scotch Plains, N.J.

[73] Assignee: Imperial Chemical Industries PLC, Millbank, England

[21] Appl. No.: 924,686

[22] Filed: Aug. 3, 1992

Related U.S. Application Data

[63] Continuation of Ser. No. 528,295, May 24, 1990.

[51] Int. Cl.$^5$ .............................................. A61K 37/02
[52] U.S. Cl. ........................................ 514/19; 514/2
[58] Field of Search ............................................ 514/19

[56] References Cited

U.S. PATENT DOCUMENTS

| | | | |
|---|---|---|---|
| 4,657,893 | 4/1987 | Krantz et al. | 514/18 |
| 4,910,190 | 3/1990 | Bergeson et al. | 514/19 |

FOREIGN PATENT DOCUMENTS

| | | |
|---|---|---|
| 0189305 | 7/1986 | European Pat. Off. |
| 0276101 | 7/1988 | European Pat. Off. |
| 0291234 | 11/1988 | European Pat. Off. |
| 0337704 | 10/1989 | European Pat. Off. |
| 0345906 | 12/1989 | European Pat. Off. |
| 0369391 | 5/1990 | European Pat. Off. |
| 0402068 | 12/1990 | European Pat. Off. |

WO 86 00 077   1/1986   PCT Int'l Appl.

OTHER PUBLICATIONS

C. T. Lee, et al., *N. Eng. J. Med.* (1981), 304, 192–196.
W. W. McGuire, et al., *J. Clin. Invest.* (1982), 69, 543–553.
M. D. Wewers, et al., *J. Clin. Invest.* (1988), 82, 1260–1267.
J. E. Weiland, et al. *Am. Rev. Respir. Dis.* (1986), 133, 218–225.
G. A. Zimmerman, et al. *Am. Rev. Respir. Dis.* (1983), 127, 290–300.
G. M. Turino, et al., *Am. J. Med.* (1974), 57, 493–505.
T. Raffin, *Hospital Practice* (Nov. 15, 1987), 65–80.
K. M. Moser, et al ., *Ann. Int. Med* (1987), 107, 560–564.
G. M. Rocker, et al., *Lancet* (1989), 8630, 120–123.

*Primary Examiner*—Charles L. Patterson, Jr.
*Attorney, Agent, or Firm*—Thomas E. Jackson

[57] ABSTRACT

There is provided a novel therapeutic agent for use in the prevention or treatment of adult respiratory distress syndrome and for use in the manufacture of a medicament for the prevention or treatment of adult respiratory distress syndrome, as well as a method of prevention or treatment of adult respiratory distress syndrome with the therapeutic agent and a method of treatment of cystic fibrosis with the therapeutic agent in combination with one or more other agents indicated for the treatment of adult respiratory distress syndrome.

18 Claims, No Drawings

THERAPEUTIC AGENT FOR THE PREVENTION OR TREATMENT OF ADULT RESPIRATORY DISTRESS SYNDROME

This is a continuation of co-pending application Ser. No. 07/528,295 filed on May 24, 1990.

This invention describes a novel therapeutic agent and, more particularly, the use of 4-(4-chlorophenylsulphonylcarbamoyl)benzoyl-L-valyl-L-proline 1(RS)-(1-trifluoroacetyl-2-methylpropyl)amide, or a pharmaceutically acceptable salt thereof, in the prevention or treatment of adult respiratory distress syndrome (hereinafter ARDS). (Although the therapeutic product is named here as 1(RS), the invention described herein includes any ratio of the 1(R)- and 1(S)-isomers of the above named compound, or the pharmaceutically acceptable salts thereof.)

ARDS is a major cause of morbidity (160,000–300,000 cases per year in the U.S.A.) and mortality (70–90% mortality) without effective therapy. ARDS is the final common pathway for a number of acute injuries, ranging from massive transfusion to neurological injury to sepsis. Lung injury is manifest as pulmonary edema, frequently hemorrhagic, with normal left-sided cardiac pressures (hence non-cardiogenic pulmonary edema). Current therapy consists of oxygen, antibiotics and supportive measures.

Neutrophil activation appears to be involved in the majority of cases of ARDS. There is evidence of elastolytic activity in secretions from ARDS patients. There is also neutrophil accumulation consistent with brisk chemotaxis and neutrophil activation. One hundred percent of patients who have undergone pulmonary thromboendarterectomy have developed ARDS localized to the re-perfused segment or lobe.

Accordingly, the present invention provides a novel therapeutic agent for use in the prophylactic or therapeutic treatment of ARDS in a mammal, especially a human, in need thereof which product comprises 4-(4-chlorophenylsulphonylcarbamoyl)benzoyl-L-valyl-L-proline 1(RS)-(1-trifluoroacetyl-2-methylpropyl)amide, or a pharmaceutically acceptable salt thereof.

As a further aspect of the invention, there is provided the use of 4-(4-chlorophenylsulphonylcarbamoyl)benzoyl-L-valyl-L-proline 1(RS)-(1-trifluoroacetyl-2-methylpropyl)amide, or a pharmaceutically acceptable salt thereof, for the manufacture of a medicament for the prophylactic or therapeutic treatment of ARDS.

As another aspect of the invention, there is provided a method of prevention or treatment of ARDS in a mammal, especially a human, in need thereof with 4-(4-chlorophenylsulphonylcarbamoyl)benzoyl-L-valyl-L-proline 1(RS)-(1-trifluoroacetyl-2-methylpropyl)amide, or a pharmaceutically acceptable salt thereof.

As yet another aspect of the invention, there is provided a method of prevention or treatment of ARDS with 4-(4-chlorophenylsulphonylcarbamoyl)benzoyl-L-valyl-L-proline 1(RS)-(1-trifluoroacetyl-2-methylpropyl)amide, or a pharmaceutically acceptable salt thereof, in combination with one or more other agents indicated for the prevention or treatment of ARDS. Such agents include, but are not limited to, antibiotics, bronchodilators, corticosteroids, oxygen, mucolytics, and mucorheologic agents.

Suitable pharmaceutically acceptable salts of 4-(4-chlorophenylsulphonylcarbamoyl)benzoyl-L-valyl-L-proline 1(RS)-(1-trifluoroacetyl-2-methylpropyl)amide (hereafter referred to as "the Compound") include, for example, those described in U.S. Pat. No. 4,910,190, for example, alkali metal and alkaline earth metal salts (such as sodium, potassium, calcium or magnesium salts), ammonium salts, and salts with organic bases affording a pharmaceutically acceptable cation. A preferred salt of the Compound for use for prevention or treatment of ARDS is, for example, a sodium or potassium salt.

The Compound and its production are described in U.S. Pat. No. 4,910,190 where it was referred to as 3(RS)-[4-[(4-chlorophenyl)sulfonylaminocarbonyl]-phenylcarbonyl ]-L-valyl-N-[3-(1,1,1-trifluoro-4-methyl-2-oxopentyl)]-L-prolinamide, but the name given hereinabove is now preferred. It is noted that Dess-Martin periodinane, described as the preferred oxidant and used in the final step for the production of the Compound in Examples 104 and 121, may in certain circumstances constitute an explosive hazard. Accordingly, it may be preferred to use an alternative oxidant for preparing the ketone from the corresponding alcohol. Alternative methods which may be useful include the use of oxalyl chloride, dimethyl sulfoxide and a tertiary amine (with the best results being obtained with 10–20 equivalents of oxidizing agent); the use of acetic anhydride and dimethyl sulfoxide; the use of chromium trioxide pyridine complex in methylene chloride; and the use of alkaline potassium permanganate solution. For example, the Compound may be obtained from the corresponding alcohol in approximately 60% yield using two equivalents of the latter oxidant.

In use, the Compound will generally be administered for prophylactic or therapeutic treatment of ARDS in the form of a conventional pharmaceutical composition, for example, as generally described in U.S. Pat. No. 4,910,190, and preferably as an intravenous injection. A formulation providing a solution containing a concentration of 10 mg/mL of the Compound and suitable for use with a nebulizer or as an injectable solution is described below in Example 1. A suitable nebulizer for use is, for example, a RETEC (trademark) nebulizer, in which the solution is nebulized with compressed air.

In general, the therapeutic agent will be administered to humans at a daily dose in the range of, for example, 1 to 20 mg/kg (especially 5 to 7 mg/kg) of the Compound intravenously. However, it readily will be understood that it may be necessary to vary the dose of therapeutic product administered in accordance with well known medical practice to take account of the nature and severity of the ARDS under treatment, concurrent therapy, and the age, weight and sex of the patient receiving treatment. It similarly will be understood that generally equivalent amounts of a pharmaceutically acceptable salt of the Compound also may be used.

The utility of the Compound, or a pharmaceutically acceptable salt thereof, in the treatment of ARDS may be demonstrated in a therapeutic intervention trial, for example as described below in Study A, in which improvement in clinical or biochemical parameters may be measured. The utility of the Compound or a pharmaceutically acceptable salt thereof, in the prevention of ARDS may be demonstrated in a prophylactic trial using the therapeutic agent for prophylaxis in patients at risk for ARDS, for example as described below in Study B, in which clinical evidence of the occurrence of ARDS, as well as improvement in clinical and biochemical parameters may be measured.

Study A in ARDS is an interventional trial using a randomized, double blind, parallel study in 24 adult patients assigned to receive 5 to 7 mg/kg/day of the Compound or vehicle (placebo) to be administered by intravenous infusion for 7 to 14 days. A formulation as described in Example 1 may be used for the treatment group, and a similar formulation without the Compound for the vehicle (control) group. Clinical outcomes which are evaluated include mortality, pulmonary hemodynamics, and supplemental oxygen requirement. Physiological sequelae, such as on pulmonary hypertension and pulmonary mechanics also may be evaluated.

Study B in ARDS is a prophylactic trial using a randomized, double-blind, parallel study design to be conducted in 10–20 patients administered 5–7 mg/kg/day of the Compound or placebo intravenously for 3 to 4 days prior to pulmonary thromboendarterectomy. Dosing is continued for 3 days to 1 week postoperatively. Clinical outcomes which are evaluated include radiographic or pulmonary hemodynamic evidence of ARDS in re-perfused lobes. In this study, the patients act as their own controls (by use of the other, nonoperated lung) for physiological measurements or for bronchoalveolar lavage fluid for biochemical measurements, such as, for example protein leakage.

The following non-limiting Example illustrates a typical formulation of the Compound for use in the method of treatment provided by the invention.

EXAMPLE 1

This example provides a formulation for 4-(4-chlorophenylsulphonylcarbamoyl)benzoyl-L-valyl-L-proline 1(RS)-(1-trifluoroacetyl-2-methylpropyl)amide, listed as a THERAPEUTIC AGENT, which provides a strength of 10 mg/mL in phosphate-buffered saline and is suitable for a nebulizer solution or for an injectable solution. A corresponding PLACEBO formulation is also provided. The prepared solutions are preferably sealed in ampules of a convenient size, for example 5 mL, and stored with refrigeration until use.

| INGREDIENT | WEIGHT PER mL | |
|---|---|---|
| | 10.0 mg | PLACEBO |
| THERAPEUTIC AGENT (1) | 10.0 mg | — |
| Dibasic Sodium Phosphate, Heptahydrate, USP | 11.97 mg | 10.74 mg |
| Monobasic Sodium Phosphate, Monohydrate, USP | 0.74 mg | 1.25 mg |
| Sodium Chloride, USP | 4.50 mg | 5.48 mg |
| 1 N Sodium Hydroxide Solution or 0.05 M Monobasic Sodium Phosphate Solution (2) | q.s. | q.s. |
| Water for Injection, USP q.s. ad | 1.0 mL (1.01 gm) | 1.0 mL (1.01 gm) |

(1) The nominal concentration of THERAPEUTIC AGENT in this formulation is 10 mg/mL. A manufacturing adjustment is made for the drug substance purity.
(2) Added to adjust pH to 7.0–7.5

MANUFACTURING DIRECTIONS: THERAPEUTIC AGENT

1. Charge approximately 90% of the required amount of Water for Injection, USP to a vessel equipped with a suitable agitation device, and connected to a heater/cooler circulation bath.
2. Adjust the temperature of the circulation bath to 30° C.
3. Charge with continuous stirring, the required amount of Dibasic Sodium Phosphate, Heptahydrate, USP and continue stirring until dissolved.
4. Charge very slowly with continuous stirring the required amount of THERAPEUTIC PRODUCT.
5. Continue to stir for approximately 30 minutes until dissolved, then decrease the temperature of the circulation bath to 25° C.
6. Charge with continuous stirring the required amount of Monobasic Sodium Phosphate, Monohydrate, USP and continue stirring until dissolved.
7. Charge with continuous stirring the required amount of Sodium Chloride, USP and continue stirring until dissolved.
8. Measure the pH and adjust to 7.0 to 7.5 with 1N Sodium Hydroxide Solution or 0.05M Monobasic Sodium Phosphate Solution, if necessary.
9. Bring the batch to final weight (calculated from specific gravity of 1.01) with Water for Injection, USP.
10. Aseptically filter the bulk solution into a suitable, sterilized filling vessel. Aseptically fill and seal the ampules.
11. Leak test ampules and visually inspect for particulate matter and other defects.

MANUFACTURING DIRECTIONS: PLACEBO

The procedure listed above is carried out with the omission of steps 2, 4 and 5, and without the need for temperature control.

What is claimed is:

1. A method of prevention or treatment of adult respiratory distress syndrome in a mammal in need thereof which comprises administering to said mammal an effective amount of 4-(4-chlorophenylsulphonylcarbamoyl)benzoyl-L-valyl-L-proline 1(RS)-(1-trifluoroacetyl-2-methylpropyl)amide, or a pharmaceutically acceptable salt thereof.

2. A method of prevention or treatment of adult respiratory distress syndrome which comprises administering an effective amount of 4-(4-chlorophenylsulphonylcarbamoyl)-benzoyl-L-valyl-L-proline 1(RS)-(1-trifluoroacetyl-2-methylpropyl)amide, or a pharmaceutically acceptable salt thereof, in combination with one or more other therapeutically active agents indicated for the prevention or treatment of adult respiratory distress syndrome.

3. A method as claimed in claim 1 wherein the pharmaceutically acceptable salt is selected from the group consisting of alkali metal and alkaline earth metal salts, ammonium salts, and salts with organic bases affording a pharmaceutically acceptable cation.

4. A method as claimed in claim 3 wherein the pharmaceutically acceptable salt is a sodium or potassium salt.

5. A method as claimed in claim 2 wherein the pharmaceutically acceptable salt is a sodium or potassium salt.

6. A method as claimed in claim 2 or 5 wherein the one or more other agents indicated for prevention or treatment of adult respiratory distress syndrome are selected from the group consisting of antibiotics, bronchodilators, corticosteroids, oxygen, mucolytics, and mucorheologic agents.

7. A method for the treatment of adult respiratory distress syndrome in a mammal in need thereof which comprises administering to said mammal an effective amount of 4-(4-chlorophenylsulphonyl-carbamoyl)-benzoyl-L-valyl-L-proline 1(RS)-(1-trifluoroacetyl-2-methyl-propyl)amide, or a pharmaceutically acceptable salt thereof.

8. A method as claimed in claim 7 wherein the pharmaceutically acceptable salt of the acid is selected from the group consisting of alkali metal and alkaline earth metal salts, ammonium salts, and salts with organic bases affording a pharmaceutically acceptable cation.

9. A method as claimed in claim 8 wherein the pharmaceutically acceptable salt is a sodium or potassium salt.

10. A method as claimed in claim 7 where in addition one or more other therapeutically active agents indicated for the treatment of adult respiratory distress syndrome is administered to said mammal.

11. A method as claimed in claim 10 wherein the one or more other therapeutically active agents are selected from the group consisting of antibiotics, bronchodilators, corticosteroids, oxygen, mucolytics and mucorheologic agents.

12. A method for the prevention of adult respiratory distress syndrome in a patient who is to undergo pulmonary thromboendarterectomy which comprises administering to said patient an effective amount of 4-(4-chlorophenylsulphonylcarbamoyl)-benzoyl-L-valyl-L-proline 1(RS)-(1-trifluoroacetyl-2-methylpropyl)amide, or a pharmaceutically acceptable salt thereof.

13. A method as claimed in claim 12 wherein the pharmaceutically acceptable salt of the acid is selected from the group consisting of alkali metal and alkaline earth metal salts, ammonium salts, and salts with organic bases affording a pharmaceutically acceptable cation.

14. A method as claimed in claim 13 wherein the pharmaceutically acceptable salt is a sodium or potassium salt.

15. A method as claimed in claim 12 where in addition one or more other therapeutically active agents indicated for the treatment of adult respiratory distress syndrome is administered to said patient.

16. A method as claimed in claim 15 wherein the one or more other therapeutically active agents are selected from the group consisting of antibiotics, bronchodilators, corticosteroids, oxygen, mucolytics and mucorheologic agents.

17. A method as claimed in claim 1, 3, or 4 wherein the mammal is a human.

18. A method as claimed in claim 7, 8, 9, 10 or 11 wherein the mammal is a human.

* * * * *